Oct. 23, 1951 G. DE RUITER Plant Pat. 1,045
ROSE PLANT
Filed Aug. 15, 1950
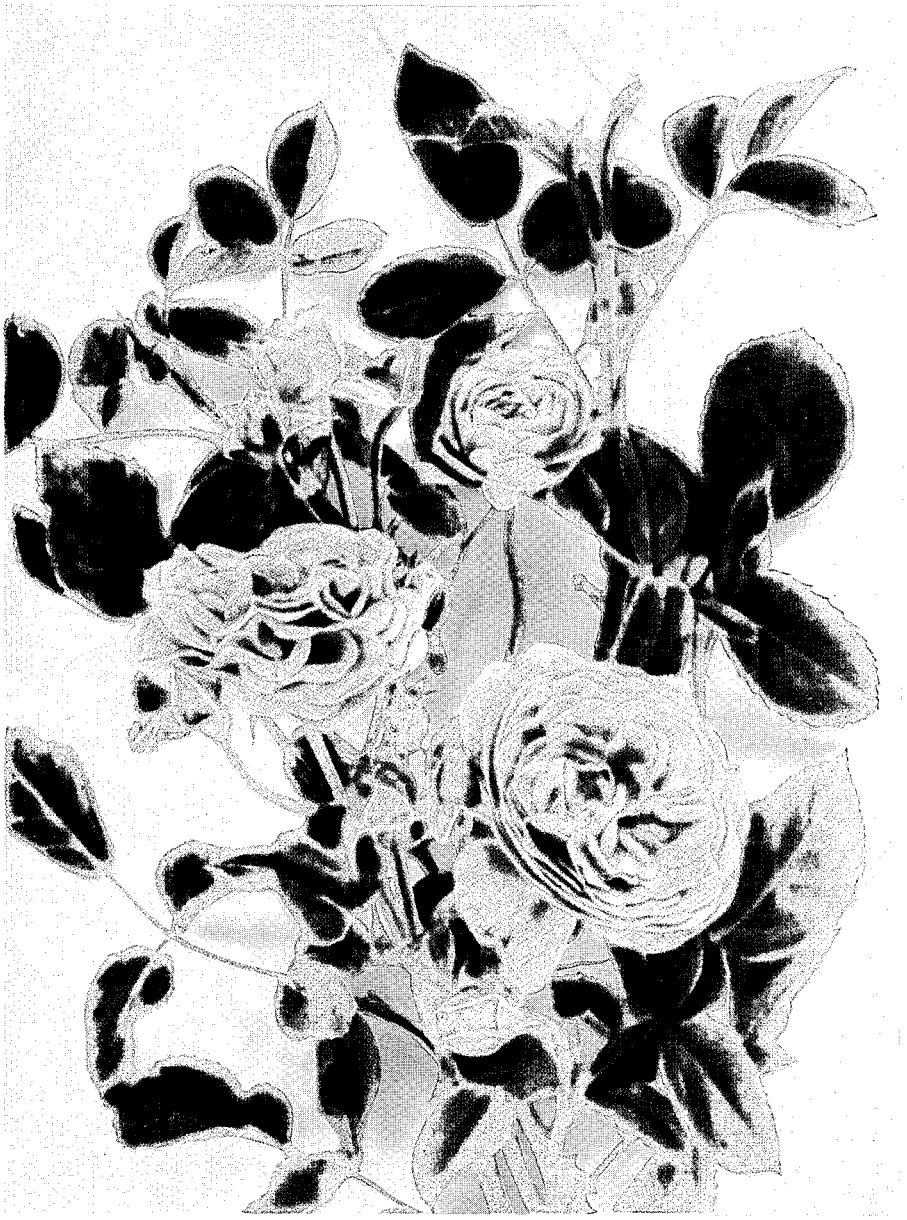
Inventor.
Gerrit de Ruiter
By: Robbs Cobb
Attorneys.

Patented Oct. 23, 1951

Plant Pat. 1,045

UNITED STATES PATENT OFFICE 1,045

ROSE PLANT

Gerrit de Ruiter, Hazerswoude, Netherlands, assignor to Jackson & Perkins Company, Newark, N. Y., a corporation of New York Application August 15, 1950, Serial No. 179,616

1 Claim. (Cl. 47—61)

The present invention relates to a new and distinct variety of rose plant of the large-flowered polyantha class, originated by crossing the variety "Orange Triumph" (unpatented) × "Anne Mette Poulsen" (Plant Patent No. 182).

The primary objective in making this cross was to obtain a better and larger flowered polyantha rose for pot plant use. This objective was fully achieved by this new variety, as will be apparent from the following description.

The parent variety "Orange Triumph" is characterized by its bright scarlet flowers, while the parent "Anne Mette Poulsen" is a large, cup-shaped floribunda, with its blooms nearly like a hybrid tea rose, and having excellent hardiness and great resistance to all kinds of weather and to mildew. In hybridizing these parent varieties, the plants of the resulting new variety kept the form and shape of "Anne Mette Poulsen," but their flowers show a distinct infusion of the color of "Orange Triumph."

This new variety is still further distinguished from its parents, as well as from other varieties by the following characteristics:

(1) The double, long-lasting flowers which retain their shape and color for four to five weeks;

(2) The Rose Red color of the flowers which are lightly overcast with Spectrum Red. This is a flower color which has long been sought in roses of the floribunda type, but never before attained;

(3) The upright, symmetrical habit of the flower bearing stems; and (4) The ease of culture of this variety as a pot plant for greenhouse forcing.

Asexual reproduction of this new variety by budding at Newark, New York, and at Pleasanton, California, shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with Ridgway's Color Standards and Nomenclature:

Parentage: Seedling.

*Seed parent.*—"Orange Triumph."

*Pollen parent.*—"Anne Mette Poulsen."

Classification:

*Botanic.*—Large-flowered polyantha.

*Commercial.*—Floribunda.

*Flower*

(Observations made from pot plants in greenhouses at Newark, New York, late in the month of March, 1950.)

Blooming habit: Recurrent—continuous.

Bud:

*Size.*—Medium.

*Form.*—Globular. Is not affected by wet or hot weather.

*Color.*—When sepals first divide—Victoria Lake, Plate 1. When petals begin to unfurl—Oxblood Red, Plate 1. When half blown—inside of petals: Carmine, Plate 1, lightly overcast with Rose Red, Plate 12; reverse of petals: Pomegranate Purple, Plate 12.

*Sepals.*—Slightly branched; curl back when petals begin to unfurl. Color—inside—Veronese Green, Plate 18; outside—Light Bice Green, Plate 17.

*Calyx.*—Shape—pear. Size—Small. Aspect—Smooth. Odor when rubbed—none. Color—Biscay Green, Plate 17.

*Peduncle.* — Length — medium. Aspect — rough. Color — Oil Green, Plate 5. Strength—erect; heavy.

*Opening.*—Bud opens up well. Is not affected by adverse weather conditions.

Bloom:

*Size.*—Large. Average size when fully expanded—3 inches to 3½ inches.

*Borne.*—Singly and several together.

*Stems.*—Medium length; normal.

*Form.*—When first open—cupped. Permanence—retains its form to the end.

*Petalage.*—Double (full but open center). Number of petals under normal conditions—30 to 35.

*Color.*—Center of flower—Rose Red, Plate 12, lightly overcast with Carmine, Plate. 1. Outer petals—Rose Red, Plate 12, overcast with Spectrum Red, Plate 1. Base of petals (aiglet)—Pale Pinkish Buff, Plate 29. Inside of petals—Rose Red, Plate 12, lightly overcast with Spectrum Red, Plate 1. Reverse of petals—Pomegranate Purple, Plate 12. General tonality from a distance—Rose Red, Plate 12, lightly overcast with Spectrum Red, Plate 1.

*Discoloration.*—General tonality at end of first day—Rose Red, Plate 1, lightly overcast with Spectrum Red, Plate 1. Second day—Rose Red, Plate 1, lightly overcast with Spectrum Red, Plate 1. Third day—Rose Red, Plate 1, overcast with Spectrum Red, Plate 1.

Petals:

*Texture*—Leathery. Is not affected by wet or hot weather.

*Appearances* — Inside — velvety. Outside — satiny.

*Form.*—Round; lightly notched.

*Arrangement.*—Informal (with "rags" in center). Petaloids in center—few; large.

*Persistence.*—Drop off cleanly.

*Fragrance.* — Moderate. Nature — fruity (Russet apple).

*Lasting quality.*—On the plant and as cut flower—long.

Genital organs:

*Stamens, anthers.*—Medium size; few. Color —Light Ochraceous Salmon, Plate 15. Arrangement—regular around styles.

*Stamens, filaments (threads).* — Medium length. Color — Pomegranate Purple, Plate 12.

*Pollen.*—Color—Pale Ochraceous Buff, Plate 15.

*Styles.*—Bunched, uneven length; medium length; thin.

*Stigmas.*—Color—Maize Yellow, Plate 4.

*Ovaries.*—All enclosed in calyx.

*Plant*

Form: Bush.

Growth: Vigorous; upright; all stems carrying straight up.

Foliage: 5 to 7 leaflets.

*Size.*—Large.

*Quantity.*—Normal.

*Color.*—New foliage—upper side—Parrot Green, Plate 6, overcast with Carmine, Plate 1; serrations Carmine, Plate 1; under side—Light Cress Green, Plate 31, overcast with Carmine, Plate 1. Old foliage—upper side—Forest Green, Plate 17; under side—Light Elm Green, Plate 17.

*Shape.*—Pointed.

*Texture.*—Upper side—glossy; under side—smooth. Ribs and veins—prominent.

*Edge.*—Serrated (saw toothed).

*Serration.*—Single; small.

*Leaf stem.*—Color—Lettuce Green, Plate 5. Under side—prickles.

*Stipules.*—Medium length; smooth.

*Disease resistance.*—Resistant.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity—on main stalks from base and on laterals from stalk—ordinary. Form—narrow base; short; straight. Color when young—Glass Green, Plate 31. Position—irregular.

*Prickles and short needles.*—None.

I claim:

A new and distinct variety of rose plant of the polyantha class, characterized as to novelty by its similarity in form and shape of the plant to its parent "Anne Mette Poulsen" (Pl. Pat. No. 182), by its double, long-lasting flowers which retain their shape and color for an unusually prolonged time, by the Rose Red lightly overcast with Spectrum Red color of its flowers, by the upright symmetrical habit of its flower bearing stems, and by its ease of culture as a pot plant for greenhouse forcing, substantially as shown and described.

GERRIT DE RUITER.

No references cited.